(12) United States Patent
Fang et al.

(10) Patent No.: US 10,209,322 B2
(45) Date of Patent: Feb. 19, 2019

(54) METHOD FOR TESTING LOCAL MAGNETOMECHANICAL COUPLING COEFFICIENT OF A MAGNETIC MATERIAL

(71) Applicants: Peking University, Beijing (CN); Jilin University, Changchun (CN)

(72) Inventors: Daining Fang, Beijing (CN); Hao Zhou, Beijing (CN); Yongmao Pei, Beijing (CN); Hongwei Zhao, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 15/534,693

(22) PCT Filed: May 18, 2015

(86) PCT No.: PCT/CN2015/079149
§ 371 (c)(1),
(2) Date: Jun. 9, 2017

(87) PCT Pub. No.: WO2016/183761
PCT Pub. Date: Nov. 24, 2016

(65) Prior Publication Data
US 2018/0081002 A1 Mar. 22, 2018

(51) Int. Cl.
*G01R 33/12* (2006.01)
*G01N 3/42* (2006.01)
*G01N 27/72* (2006.01)

(52) U.S. Cl.
CPC .............. *G01R 33/12* (2013.01); *G01N 3/42* (2013.01); *G01N 27/72* (2013.01)

(58) Field of Classification Search
None
See application file for complete search history.

(56) References Cited

U.S. PATENT DOCUMENTS

| | | | | |
|---|---|---|---|---|
| 8,599,383 B2* | 12/2013 | Teitell | ...................... | G01J 3/453 356/451 |
| 9,672,858 B2* | 6/2017 | Watanabe | ............ | G11B 5/7305 |
| 2005/0122527 A1* | 6/2005 | Boccara | ................. | G02B 21/22 356/450 |
| 2005/0195405 A1* | 9/2005 | Ina | ...................... | G03F 7/70633 356/497 |
| 2005/0200856 A1* | 9/2005 | Groot | ................. | G01B 11/2441 356/512 |

(Continued)

*Primary Examiner* — Peter J Macchiarolo
*Assistant Examiner* — Jermaine L Jenkins
(74) *Attorney, Agent, or Firm* — SV Patent Service

(57) ABSTRACT

A method for testing a local magnetomechanical coupling coefficient of a magnetic material includes defining a square of a local magnetomechanical coupling coefficient $k_{IT}$ as a the ratio of a magnetic energy stored in a magnetic material to an input reversible mechanical work, and characterizing the local magnetomechanical coupling coefficient of the magnetic material by measuring nano-indentation load-depth curves of the magnetic material under both situations of a saturated magnetic field and an unsaturated magnetic field. The method is simple in operation and has the advantages in local performance test of composite materials and other heterogeneous materials and also in small-scale performance test of nano-films.

7 Claims, 4 Drawing Sheets

(56) References Cited

U.S. PATENT DOCUMENTS

2005/0248770 A1\* 11/2005 Lin .................... G01B 11/2441
356/489
2012/0164745 A1\* 6/2012 Fu ........................ G01N 21/658
436/164

\* cited by examiner

METHOD FOR TESTING LOCAL MAGNETOMECHANICAL COUPLING COEFFICIENT OF A MAGNETIC MATERIAL

TECHNICAL FIELD

The present invention relates to the field of micro-scale physical measurement of magnetic material, and specifically, to a method for testing a local magnetomechanical coupling coefficient of a magnetic material, and in particular, to the proposal a concept of the local magnetomechanical coupling coefficient and a test method thereof based on nano-indentation.

BACKGROUND OF THE INVENTION

Ferromagnetic materials, magnetoelectric composite materials and other functional materials are often used as a variety of transducers and sensors, etc. The device designers need to know the magnetomechanical coupling characteristics of such a material in order to carry out a reasonable functional design and performance optimization. At present, the magnetomechanical coupling performances of the material are generally quantified by the magnetomechanical coupling coefficient, whose square is equal to the ratio of the output mechanical energy of the material to the input magnetic field energy. This physical quantity can be measured through a three-parameter method or a resonance method. But these two methods can only obtain the average performance of the whole sample, and cannot obtain local performances. Therefore, these methods cannot meet the test requirements for the small-scale physical properties of the heterogeneous materials and nano-films.

SUMMARY OF THE INVENTION

The present invention aims at providing a method for testing a local magnetomechanical coupling coefficient of a magnetic material. The concept of local electromechanical coupling coefficient and the testing method are proposed thereof by analyzing the energy conversion in a nano-indentation process. The method is simple in operation and has advantages in testing local performance of composite materials and other heterogeneous materials and also in testing small-scale performance of nano-films.

The technical solution of the present invention is as follows:

An indentation test is carried out for a magnetic material. The experimental curves of a nano-indentation test are shown in FIG. 1: the initial load and indentation depth was zero; the load gradually increased to the maximum value to form the loading curve; and then gradually reduced to zero to form the unloading curve. The projection area of the loading curve to the horizontal axis is the total work $W_{tot}$. The projection area of the unloading curve to the horizontal axis is the reversible mechanical work $W_{re}$ (referred to reversible work), the total work minus the reversible work is the plastic work $W_{pla}$.

Firstly, in the present invention, an indentation reversible work $W_{re}$ of the magnetic material is divided into two parts: an elastic energy $W_{ela}$ and a magnetic energy $W_{mag}$. Then, the concept of a local electromechanical coupling coefficient $k_{IT}$ is proposed. The local electromechanical coupling coefficient is defined as the square root of the ratio of the magnetic energy $W_{mag}$ stored in the magnetic material to the input reversible mechanical work $W_{re}$, which is expressed by an equation as follows:

$$k_{IT} = \sqrt{\frac{W_{mag}}{W_{re}}} = \sqrt{\frac{W_{mag}}{W_{ela} + W_{mag}}} \quad (1)$$

In the situations of applying a saturated magnetic field and an unsaturated magnetic field, the energy conversion of the magnetic material during the indentation process is as follows:

a) In the situation of applying the saturated magnetic field: the magnetic material changes from a multi-domain magnetic state to a single domain state, the direction of the microscopic magnetization within the material is the same as that of the applied magnetic field. When the magnetic field is sufficiently strong, the deformation resulted from magnetization rotation in the indentation process can be ignored, thus the change of the magnetic interaction energy during the indentation process can be ignored. The indentation total work $W_{tot}^s$ is only converted to two parts: the elastic energy $W_{re}^s$ and the plastic work $W_p^s$ note: the superscripts indicates parameters under the condition of magnetic saturation); in other words, the reversible work $W_{re}^s$ equals to the elastic work $W_{ela}^s$. The unloading curve and the loading curve in FIG. 1 are integrated, to obtain the reversible work $W_{re}^s$ and the total work $W_{tot}^s$. Their ratio is denoted by C, which is expressed by the following equation:

$$\frac{W_{re}^s}{W_{tot}^s} = \frac{W_{ela}^s}{W_{ela}^s + W_{pla}^s} = C \quad (2)$$

b) In the situation of applying a non-saturating magnetic field: the magnetic material is in the multi-domain state, in which the micro-magnetization orientation is not uniform. The indentation causes realignments in the micro-magnetization therein, resulting in significant changes in the magnetic interactions in the system. The indentation total work $W_{tot}^u$ is converted into three parts: the elastic energy $W_{ela}^u$, the magnetic energy $W_{mag}^u$ and the plastic work $W_{pla}^u$ (Note: the subscript u represents parameters in the situation of non-magnetic-saturation), wherein the elastic energy $W_{ela}^u$ and the magnetic energy $W_{mag}^u$ constitute unloading work $W_{re}^u$. The unloading curve and the loading curve in FIG. 1 are integrated, to obtain the unloading work $W_{re}^u$ and the total work $W_{tot}^u$. Their ratio is denoted by d, which is expressed by the following equation:

$$\frac{W_{re}^u}{W_{tot}^u} = \frac{W_{ela}^u + W_{mag}^u}{W_{ela}^u + W_{mag}^u + W_{pla}^u} = d \quad (3)$$

c) Since the magnetic field mainly affects the orientation distribution of the micro-magnetization of the material and the magnetization rotation evolution during indentation process, the elasticity and the plasticity are determined by the interaction force and shear strength of the bonds in the lattice, and do not significantly change in response to an external magnetic field. Thus it may be assumed that the ratios of elastic energy and the plastic work are equal in the situations of applying the unsaturated magnetic field and applying the saturated magnetic field, that is:

$$\frac{W_{ela}^u}{W_{ela}^u + W_{pla}^u} = \frac{W_{ela}^s}{W_{ela}^s + W_{pla}^s} = C \quad (4)$$

The ratio of the magnetic energy and the elastic energy in the situation of the unsaturated magnetic field may be obtained through the equations (2)-(4):

$$\frac{W^u_{mag}}{W^u_{ela}} = \frac{d-C}{C(1-d)} \quad (5)$$

Substituting Equation (5) into the equation (1), the expression of the local magnetomechanical coupling coefficient of the magnetic material in the situation of the non-saturation-magnetic field may be expressed as follows:

$$k_{IT} = \sqrt{\frac{W^u_{mag}}{W^u_{ela} + W^u_{mag}}} = \sqrt{\frac{d-C}{d(1-C)}} \quad (6)$$

Based on the concept of the local magnetomechanical coupling coefficient and the analysis of the energy conversion during the indentation process in the situations of two kinds of magnetic fields, the present disclosure proposes a method for testing a local magnetomechanical coupling coefficient of a magnetic material, comprising the steps of (as shown in FIG. 2):

1) applying a saturated magnetic field to bring the magnetic material to a single domain state, measuring nano-indentation load-depth curves of the magnetic material, and integrating the unloading curve and the loading curve thereof;

2) applying an unsaturated magnetic field to bring the magnetic material to a multi-domain state, and measuring nano-indentation load-depth curves of the magnetic material;

3) obtaining the local magnetomechanical coupling coefficient of the magnetic material using Equation (6):

$$k_{IT} = \sqrt{\frac{d-C}{d(1-C)}}$$

In step 1) and step 2) described above, the magnetic material may be placed between two permanent magnets. A magnetic field strength applied to the magnetic material is adjusted by adjusting the distance between the two permanent magnets. In one implementation, preferably, the applied magnetic field strength is measured using a Hall probe.

In step 1) and step 2) described above, an indenter connected to a piezoelectric actuator can be pressed into the magnetic material. A load signal and a depth signal of the indentation are simultaneously measured through a load sensor and a displacement sensor respectively during the indentation loading process and the indentation unloading process.

The presently disclosed method for testing the local magnetomechanical coupling coefficient is particularly suitable for testing composite materials and other heterogeneous magnetic materials, such as TbDyFe/PMN-PT and FeGa/PZT and other layered electromagnetic composite material. In addition, the presently disclosed test method is also convenient for testing the properties of magnetic thin film materials having a thickness in nano-scale.

The present invention has the following advantages and notable effects that: (1) the concept of local electromechanical coupling coefficient and the testing method thereof based on nano-indentation are proposed for the first time; (2) the method is simple for operation; (3) it has advantages in local performance test of composite materials and heterogeneous materials; (4) it also has advantages in small-scale performance test of nano-films.

DETAILED DESCRIPTION OF THE INVENTION

The technical details and embodiments of the present invention will be further described in the following with reference to the accompanying drawings.

Figure 1:
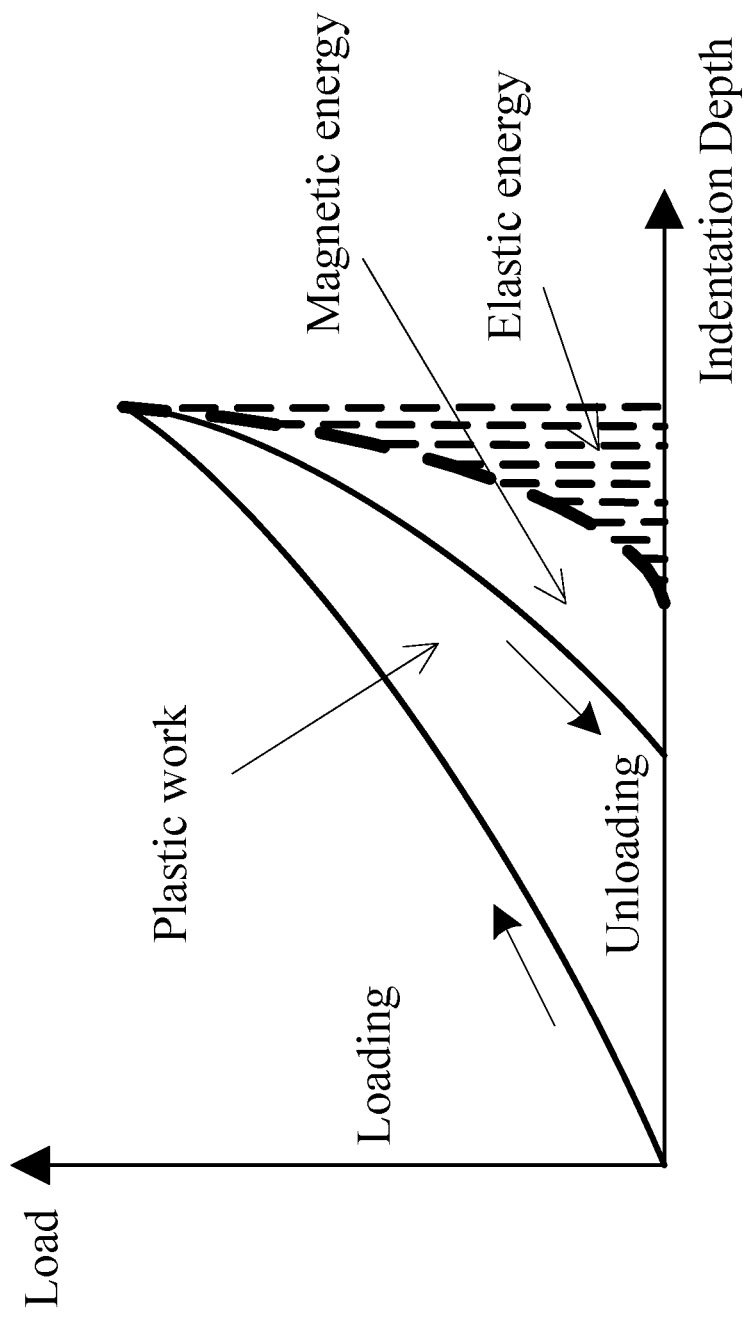
FIG. 1 is a schematic diagram of energy conversions in a magnetic material undergoing an indentation process.
Figure 2:
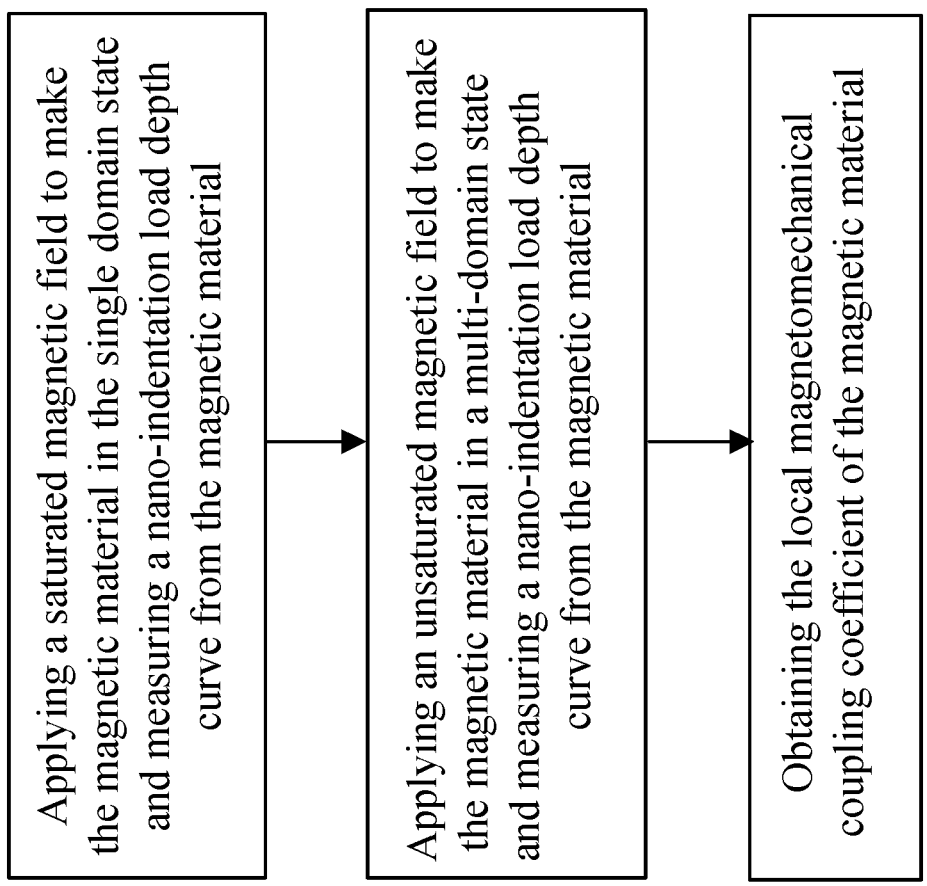
FIG. 2 is a flow chart of for testing a local magnetomechanical coupling coefficient in accordance with some embodiments of the present invention.
Figure 3:
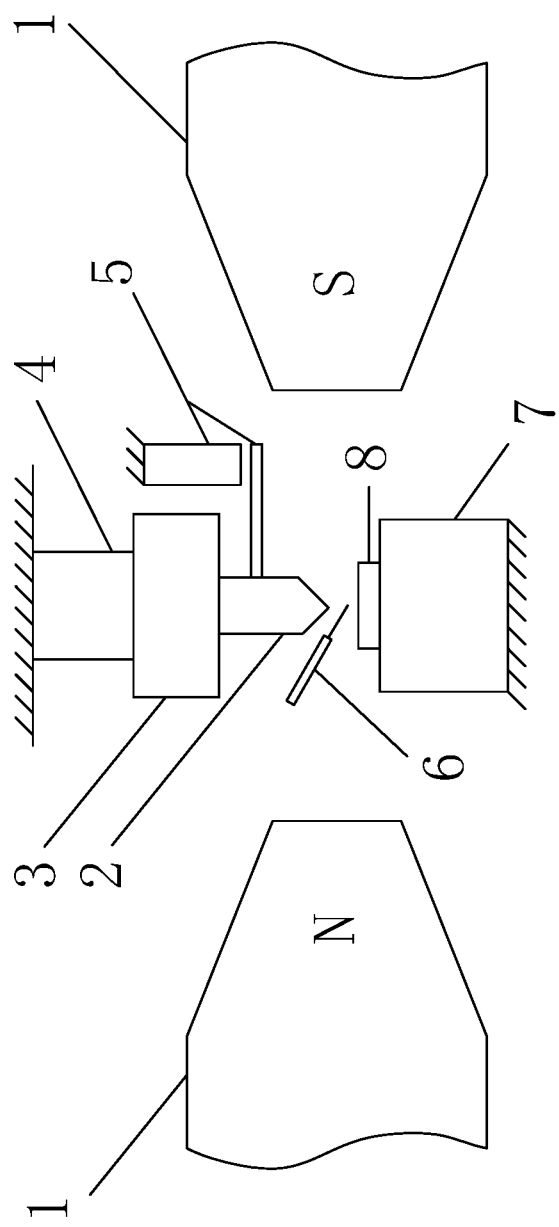
FIG. 3 is a schematic diagram of a device for testing the local magnetomechanical coupling coefficient in accordance with some embodiments of the present invention, in which part numbers are: 1—NdFeB permanent magnet; 2—indenter; 3—load sensor; 4—piezoelectric actuator; 5—displacement sensor; 6—Hall probe; 7—nonmagnetic sample stage; 8—magnetic sample.

In some embodiments, referring to FIG. 3, a device for testing a local magnetomechanical coupling coefficient of a magnetic material mainly includes an NdFeB permanent magnet 1; an indenter 2; a load sensor 3; a piezoelectric actuator 4; a displacement sensor 5; a Hall probe 6; a nonmagnetic sample stage 7, and a magnetic sample 8.

In one example, the magnetic sample 8 can be specifically a nickel single crystal material. The sample has a size of 5×5×0.2 mm$^3$ (length× width× thickness) and a thickness direction is the [111] crystal orientation. The distance between the two NdFeB permanent magnets 1 can be adjusted, to vary the magnetic field strength applied to the sample. The applied magnetic field strength is measured by the Hall probe 6. The piezoelectric actuator 4 drives the indenter 2 to press in magnetic sample 8. The load sensor 3 and the displacement sensor 5 respectively measured the load (P) and a depth (h) signal 5 during the indentation loading process and the indentation unloading process.

Figure 4:
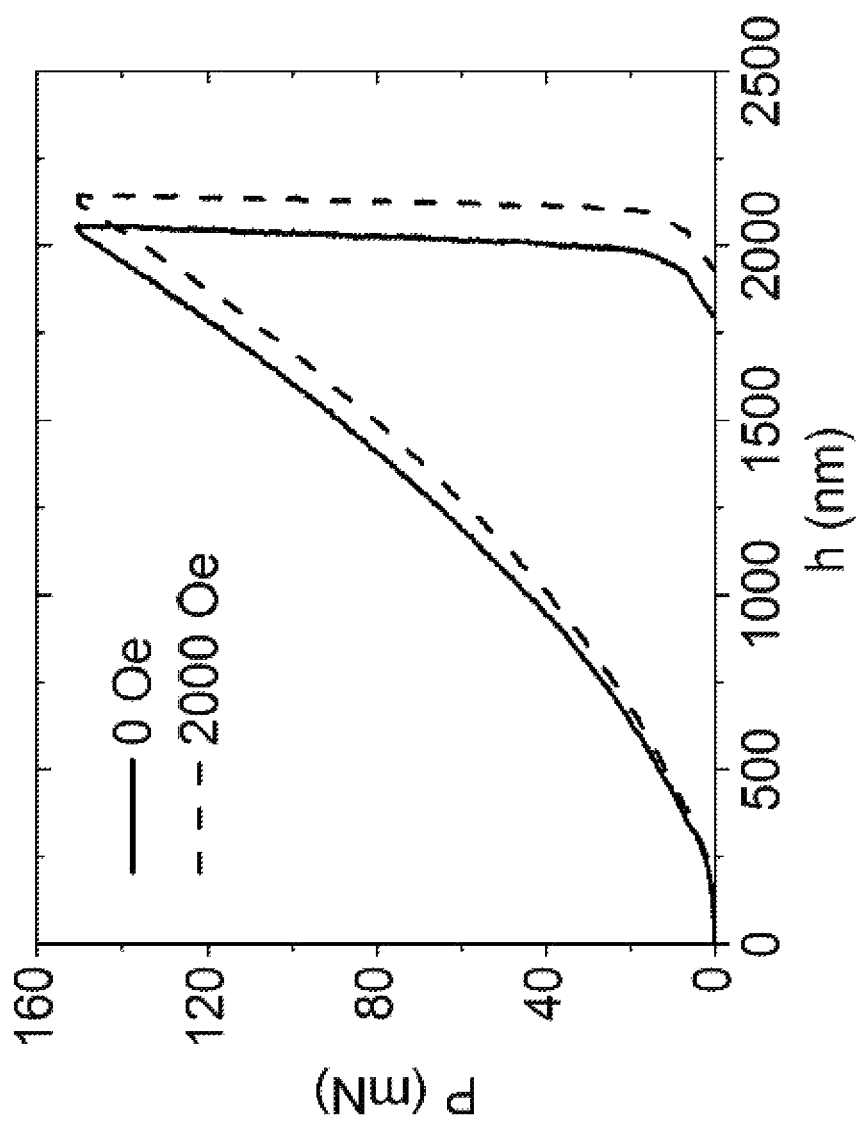
FIG. 4 shows load-depth curves obtained from nano-indentation of a tested nickel single crystal sample in accordance with some embodiments of the present invention.

Firstly, the distance between the two NdFeB permanent magnets 1 was adjusted, until the magnetic field strength measured by the Hall probe 6 reached 2000 Oe. At this time, the nickel single crystal sample was in the single domain state. A load-depth curve thereof was measured, as shown in FIG. 4.

Then, the distance between the two NdFeB permanent magnets 1 was adjusted, until the magnetic field strength measured by the Hall probe 6 reached 0 Oe. At this time, the nickel single crystal sample was in the multi-domain state. A load-depth curve thereof was measured, as shown in FIG. 4.

Finally, indentation curves obtained in the two situations of the magnetic saturation and the non-magnetic-saturation were integrated. The ratios of unloading work and total work the in the two states were respectively obtained. An average of 50 to 60 experiments was taken, in order to reduce the test error caused by the instrument thermal drift and the environmental noise. According to the theoretical equation (6), the local magnetomechanical coupling coefficient of the nickel single crystal material at zero magnetic field is obtained as follow:

$$k_{IT} = \sqrt{\frac{d-C}{d(1-C)}} = 0.62$$

The experimental result shows that the magnetomechanical coupling coefficient (0.62) of the micro-scale contact deformation is much larger than that of the macroscopic uniaxial deformation (about 0.2).

What is claimed is:

1. A method for testing a local magnetomechanical coupling coefficient of a magnetic material, comprising:
    defining a local magnetomechanical coupling coefficient $k_{IT}$ as a square root of a ratio of a magnetic energy $W_{mag}$ to an input reversible mechanical work $W_{re}$, wherein the magnetic energy $W_{mag}$ is stored in a magnetic material, and
    determining $k_{IT}$ of the magnetic material comprising the following steps:
    1) applying a saturated magnetic field to transform the magnetic material to a single domain state; measuring nano-indentation load-depth curves comprising a first unloading curve and a first loading curve of the magnetic material; integrating the first unloading curve and the first loading curve as functions of depth thereof respectively to obtain a reversible work $W_{re}^s$ and a total work $W_{tot}^s$, in the single domain state; and recording a ratio of the reversible work $W_{re}^s$ to the total work $W_{tot}^s$ as C;
    2) applying an unsaturated magnetic field to transform the magnetic material to a multi-domain state; measuring nano-indentation load-depth curves comprising a second unloading curve and a second loading curve of the magnetic material; integrating the second unloading curve and the second loading curve as functions of depth thereof respectively to obtain an unloading work $W_{re}^u$ and a total work $W_{tot}^u$ in the multi-domain state; and recording the ratio of the unloading work $W_{re}^u$ to the total work $W_{tot}^u$ as d; and
    3) obtaining the local magnetomechanical coupling coefficient of the magnetic material according to the following equation:

$$k_{IT} = \sqrt{\frac{d-C}{d(1-C)}}.$$

2. The method of claim 1, wherein in step 1) and step 2), the magnetic material is placed between two permanent magnets, the method further comprising:
    varying a magnetic field strength applied to the magnetic material by adjusting a distance between the two permanent magnets.

3. The method of claim 2, wherein in step 1) and step 2), wherein the applied magnetic field strength is measured by a Hall probe.

4. The method of claim 1, wherein step 1) and step 2) further comprise:
    pressing an indenter into the magnetic material, wherein the indenter is connected to a piezoelectric actuator;
    simultaneously measuring a load signal and a depth signal of an indentation respectively by a load sensor and a displacement sensor during an indentation loading process; and
    simultaneously measuring a load signal and a depth signal of an indentation respectively by a load sensor and a displacement sensor during an indentation unloading process.

5. The method of claim 1, wherein the magnetic material comprises a non-homogeneous magnetic material.

6. The method of claim 5, wherein the magnetic material comprises a layered electromagnetic composite material.

7. The method of claim 1, wherein the magnetic material comprises a magnetic thin film material in nano-scale.

* * * * *